US00PP19198P2

(12) United States Plant Patent
Oide

(10) Patent No.: US PP19,198 P2
(45) Date of Patent: Sep. 9, 2008

(54) ***AZALEA* PLANT NAMED 'ORYU'**

(50) Latin Name: ***Rhododendron pulchrum*× *Rhododendron simsii***
Varietal Denomination: Oryu

(75) Inventor: Masao Oide, Tochigi (JP)

(73) Assignee: Suntory Flowers Ltd., Tokyo (JP)

( * ) Notice: Subject to any disclaimer, the term of this patent is extended or adjusted under 35 U.S.C. 154(b) by 0 days.

(21) Appl. No.: 11/807,285

(22) Filed: May 26, 2007

(51) Int. Cl.
*A01H 5/00* (2006.01)

(52) U.S. Cl. ..... Plt./238
(58) Field of Classification Search ..... Plt./238
See application file for complete search history.

*Primary Examiner*—Kent L. Bell
*Assistant Examiner*—Annette H Para
(74) *Attorney, Agent, or Firm*—C. A. Whealy

(57) ABSTRACT

A new and distinct cultivar of *Azalea* plant named 'Oryu', characterized by its upright plant habit; freely branching habit; freely flowering habit; single light green to white-colored flowers; and excellent postproduction longevity.

1 Drawing Sheet

Botanical designation: *Rhododendron pulchrum*× *Rhododendron simsii.*
Cultivar denomination: 'ORYO'.

BACKGROUND OF THE INVENTION

The present invention relates to a new and distinct cultivar of *Azalea*, botanically known as *Rhododendron pulchrum*× *Rhododendron simsii,* and hereinafter referred to by the name 'Oryu'.

The new *Azalea* is a product of a planned breeding program conducted by the Inventor in Tochigi, Japan. The objective of the breeding program is to create new *Azalea* varieties having unique and attractive flower color.

The new *Azalea* originated from a cross-pollination made by the Inventor in June, 1985, in Tochigi, Japan, of an unnamed proprietary selection of *Rhododendron pulchrum,* not patented, as the female, or seed, parent with an unnamed proprietary selection of *Rhododendron simsii,* not patented, as the male, or pollen, parent. The new *Azalea* was discovered and selected by the Inventor as a flowering plant within the progeny of the stated cross-pollination in a controlled environment in Tochigi, Japan.

Asexual reproduction of the new *Azalea* by terminal cuttings taken in a controlled environment in Tochigi, Japan has shown that the unique features of this new *Azalea* are stable and reproduced true to type in successive generations.

SUMMARY OF THE INVENTION

The new *Azalea* has not been observed under all possible environmental conditions. The phenotype may vary somewhat with variations in environment such as temperature, daylength and/or light intensity without, however, any variance in genotype. The following traits have been repeatedly observed and are determined to be the unique characteristics of 'Oryu'. These characteristics in combination distinguish 'Oryu' as a new and distinct cultivar:

1. Upright plant habit.
2. Freely branching habit.
3. Freely flowering habit.

4. Single light green to white-colored flowers.
5. Excellent postproduction longevity.

Plants of the new *Azalea* differ from plants of the female parent selection in the following characteristics:

1. Plants of the new *Azalea* have larger leaves than plants of the female parent selection.
2. Plants of the new *Azalea* have smaller flowers than plants of the female parent selection.
3. Plants of the new *Azalea* and the female parent selection differ in flower color as plants of the female parent selection have pale greenish yellow-colored flowers.

Plants of the new *Azalea* differ from plants of the male parent selection in the following characteristics:

1. Plants of the new *Azalea* have larger leaves than plants of the male parent selection.
2. Plants of the new *Azalea* have smaller flowers than plants of the male parent selection.
3. Plants of the new *Azalea* and the male parent selection differ in flower color as plants of the male parent selection have pale pink-colored flowers.

Plants of the new Azalea can be compared to the plants of the cultivar Miyonosakae, not patented. In side-by-side comparisons conducted in Tochigi, Japan, plants of the new *Azalea* differed from plants of the cultivar Miyonosakae in the following characteristics:

1. Plants of the new *Azalea* were more upright and taller than and not as broad as plants of the cultivar Miyonosakae.
2. Plants of the new *Azalea* had smaller leaves and flowers than plants of the cultivar Miyonosakae.
3. Plants of the new *Azalea* and the cultivar Miyonosakae differed in flower color as plants of the cultivar Miyonosakae had pink-colored flowers.
4. Plants of the new *Azalea* had longer postproduction longevity than plants of the cultivar Miyonosakae.

BRIEF DESCRIPTION OF THE PHOTOGRAPHS

The accompanying colored photographs illustrate the overall appearance of the new *Azalea*. These photographs show the colors as true as it is reasonably possible to obtain in colored reproductions of this type. Colors in the photographs may differ slightly from the color values cited in the detailed botanical description, which accurately describe the colors of the new *Azalea*.

The photograph at the top of the sheet comprises a side perspective view of the typical flowering plant of 'Oryo'.

The photograph at the bottom of the sheet is a close-up view of typical flowers of 'Oryu'.

DETAILED BOTANICAL DESCRIPTION

The aforementioned photographs and following observations and measurements describe plants grown in Tochigi, Japan in 12-cm containers, in a polyethylene-covered greenhouse during the winter and under commercial production conditions. During the production of the plants, day temperatures ranged from 15° C. to 35° C. and night temperatures ranged from 5° C. to 25° C. Plants used for the photographs and description were about three years old. In the following description, color references are made to The Royal Horticultural Society Colour Chart, 2001 Edition, except where general terms of ordinary dictionary significance are used.

Botanical classification: *Rhododendron pulchrum*× *Rhododendron simsii* 'Oryu'.

Parentage:

*Female, or seed, parent.*—Unnamed proprietary selection of *Rhododendron pulchrum,* not patented.

*Male, or pollen, parent.*—Unnamed proprietary selection of *Rhododendron simsii,* not patented.

Propagation:

*Type.*—By terminal vegetative cuttings.

*Time to initiate roots.*—About 40 days at temperatures of 20° C.

*Time to produce a rooted young plant.*—About 100 days at temperatures of 20° C.

*Root description.*—Fine, fibrous, and white in color.

*Rooting habit.*—Freely branching.

Plant description:

*Plant form and growth habit.*—Perennial, evergreen; upright plant habit; moderately vigorous growth habit. Densely foliated; full and bushy plants. Freely flowering habit with numerous single flowers per plant.

*Branching habit.*—Freely branching habit; about 23 lateral branches develop per plant.

*Plant height, soil level to top of flowers.*—About 50 cm.

*Plant diameter, area of spread.*—About 36.5 cm.

*Lateral branch description.*—Diameter: About 1.8 mm. Internode length: About 8 mm. Strength: Strong. Texture, developing: Pubescent, fine reddish brown hairs. Texture, mature: Woody. Color, developing: N144A. Color, mature: 165B.

*Foliage description.*—Arrangement. Alternate, single. Length: About 5.4 cm. Width: About 2.3 cm. Shape: Lanceolate. Apex: Acute to obtuse. Base: Cuneate. Margin: Entire. Venation pattern: Pinnate. Texture, upper and lower surfaces: Pubescent. Color: Developing foliage, upper surface: 144A. Developing foliage, lower surface: 138A. Fully expanded foliage, upper surface: Close to N144A; venation, 145B. Fully expanded foliage, lower surface: 138B; venation, 145B.

*Petiole.*—Length: About 9 mm. Diameter: About 0.9 mm. Texture, upper and lower surfaces: Pubescent. Color, upper and lower surfaces: 145B.

Flower description:

*Natural flowering season.*—Plants of the new Azalea typically flower in the spring after sufficient cool period. Flowers not persistent.

*Flower arrangement and appearance.*—Flowers arranged singly at terminals with usually about two or three flowers per apex; freely flowering habit. Flowers face upward or outward. Flowers rotate and rose-like; single flower form.

*Postproduction longevity.*—Excellent postproduction longevity; plants maintain good flower substance for about four weeks.

*Fragrance.*—None detected.

*Flower diameter.*—About 7 cm.

*Flower depth.*—About 3.6 cm.

*Flower bud* (*before showing color*).—Length: About 1.5 cm. Diameter: About 9 mm. Shape: Ovoid. Color: 145D.

*Petals.*—Arrangement: Single flower form; single whorl of five imbricate petals; petals fused at the base. Length: About 2.5 cm. Width: About 2.8 cm. Shape: Roughly spatulate to ovate with rounded to emarginate apex. Margin: Entire. Texture, upper and lower surfaces: Smooth, glabrous; velvety. Color: When opening and fully opened, upper surface: 150D; towards the base, 2D; spots, N144C. Color becoming closer to 155A with development. When opening and fully opened, lower surface: 150D; towards the base, 2D.

*Sepals.*—Arrangement: Five fused in a single whorl. Length: About 8 mm to 10 mm. Width: About 3 mm to 6 mm. Shape: Ovate. Apex: Obtuse. Base: Fused. Texture, upper surface: Smooth, glabrous. Texture, lower surface: Pubescent. Color, upper surface: 143B. Color, lower surface: 143B to 143C.

*Peduncles.*—Length: About 1.7 cm. Diameter: About 2 mm. Angle: Upright or outward. Strength: Flexible; strong. Texture: Smooth, glabrous. Color: N144D.

*Reproductive organs.*—Androecium: Quantity per flower: About five to ten. Stamen length: About 1.5 mm to 2.5 mm. Anther shape: Ellipsoidal. Anther size: About 1 mm by 3.5 mm. Anther color: Close to 155D. Pollen amount: Scarce. Gynoecium: Quantity of pistils per flower: Typically one. Pistil length: About 2.4 cm. Style color: 181C; towards the base, 144D. Stigma shape: Transversely ellipsoidal. Stigma diameter: About 1 mm. Stigma color: 144A. Ovary color: 144B.

*Seed/fruit.*—Seed and fruit development have not been observed.

Weather/temperature tolerance: Plants of the new *Azalea* have been observed to be tolerant to rain and wind and to tolerate temperatures from about 5° C. to about 35° C.

Disease/pest resistance: Plants have not been observed to be resistant to pathogens and pests common to *Azaleas*.

It is claimed:

1. A new and distinct cultivar of *Azalea* plant named 'Oryu' as illustrated and described.

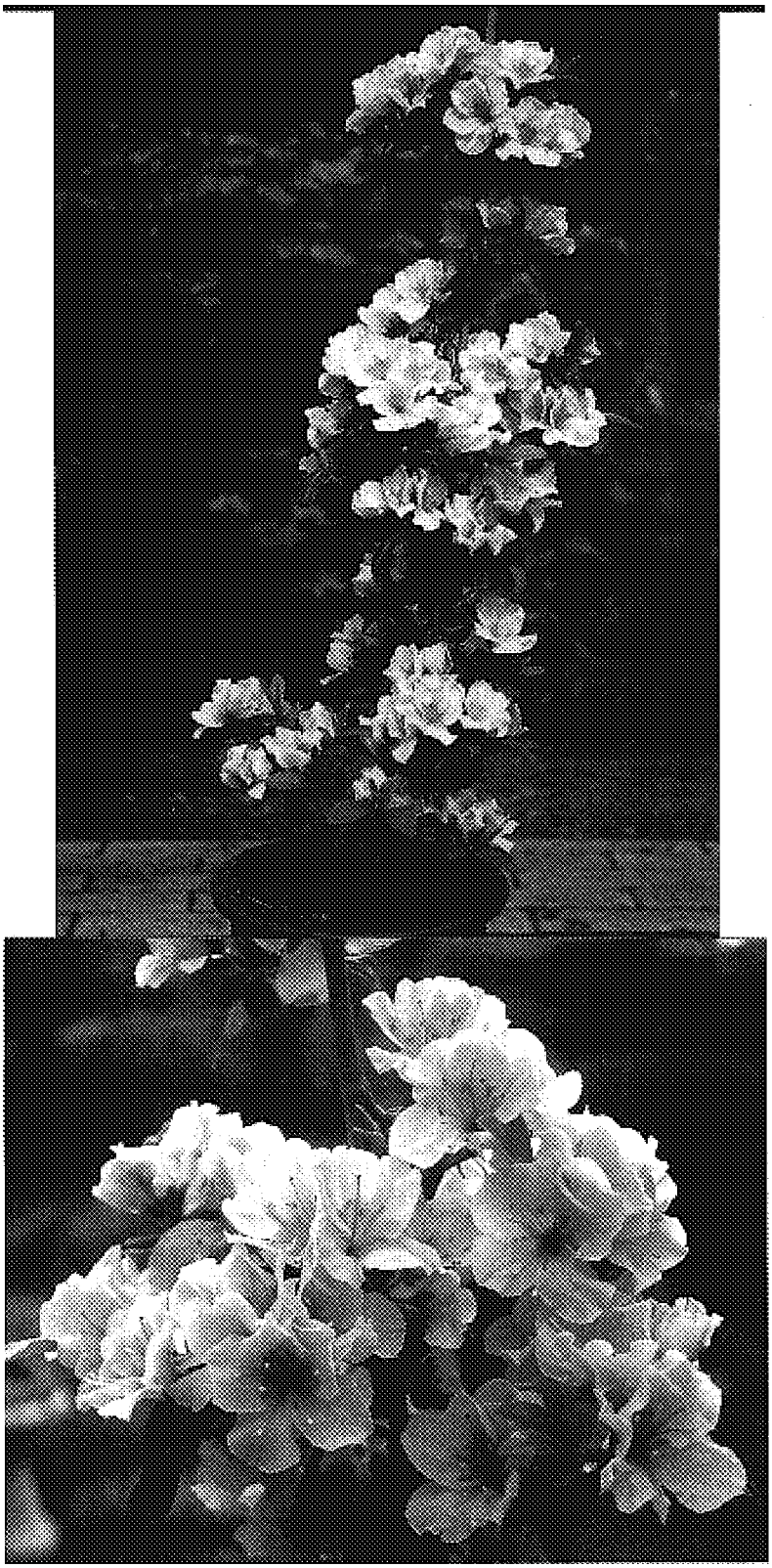

* * * * *